(12) United States Patent
Pierson, III

(10) Patent No.: US 6,200,323 B1
(45) Date of Patent: *Mar. 13, 2001

(54) BONE DEPTH RESECTION GUIDE AND METHOD

(76) Inventor: Raymond H. Pierson, III, 62 W. Columbia St., Suite C, Orlando, FL (US) 32806

( * ) Notice: Subject to any disclaimer, the term of this patent is extended or adjusted under 35 U.S.C. 154(b) by 0 days.

This patent is subject to a terminal disclaimer.

(21) Appl. No.: 09/335,110

(22) Filed: Jun. 17, 1999

Related U.S. Application Data

(63) Continuation-in-part of application No. 09/205,593, filed on Dec. 4, 1998, now Pat. No. 6,042,584.

(51) Int. Cl.$^7$ .................................................... A61B 17/58
(52) U.S. Cl. .............................. 606/102; 606/73; 606/77; 411/5
(58) Field of Search .................................. 606/73, 76, 77, 606/102, 104; 411/5

(56) References Cited

U.S. PATENT DOCUMENTS

| | | |
|---|---|---|
| 3,343,443 | 9/1967 | Moore . |
| 3,915,162 | 10/1975 | Miller . |
| 4,005,527 | 2/1977 | Wilson et al. . |
| 4,421,112 | 12/1983 | Mains et al. . |
| 4,815,467 | 3/1989 | Chestnut . |
| 4,978,351 | 12/1990 | Rozas . |
| 5,122,146 * | 6/1992 | Chapman et al. ................. 606/102 |
| 5,129,904 | 7/1992 | Illi . |
| 5,129,906 | 7/1992 | Ross et al. . |
| 5,169,400 | 12/1992 | Muhling et al. . |
| 5,562,704 | 10/1996 | Tamminmaki et al. . |
| 5,643,274 * | 7/1997 | Sander et al. ..................... 606/104 |
| 5,895,396 | 4/1999 | Day et al. . |
| 5,904,685 * | 5/1999 | Walawalkar ........................ 606/73 |
| 5,938,662 * | 8/1999 | Rinner ................................. 606/73 |
| 6,042,584 * | 3/2000 | Pierson, III ....................... 606/102 |

* cited by examiner

Primary Examiner—Michael Buiz
Assistant Examiner—Julian W. Woo
(74) Attorney, Agent, or Firm—Allen, Dyer, Doppelt, Milbrath & Gilchrist, P.A.

(57) ABSTRACT

A gauge for measuring bone thickness includes an elongated pin for insertion into a bore through a bone section. The pin has a length sufficient to span the entire bone section with a distal tip protruding therefrom. The pin further has a length measurement indicator disposed along an outer surface, such as a series of colored bands or indicia, the visualization of which communicates bone thickness. In a particular embodiment a protrusion extending away from the pin's outer surface is provided to retain the pin within the bore. A cannula may be provided for facilitating the introduction of the pin into the bone section. Methods are also described for measuring bone thickness and for contouring bone.

42 Claims, 8 Drawing Sheets

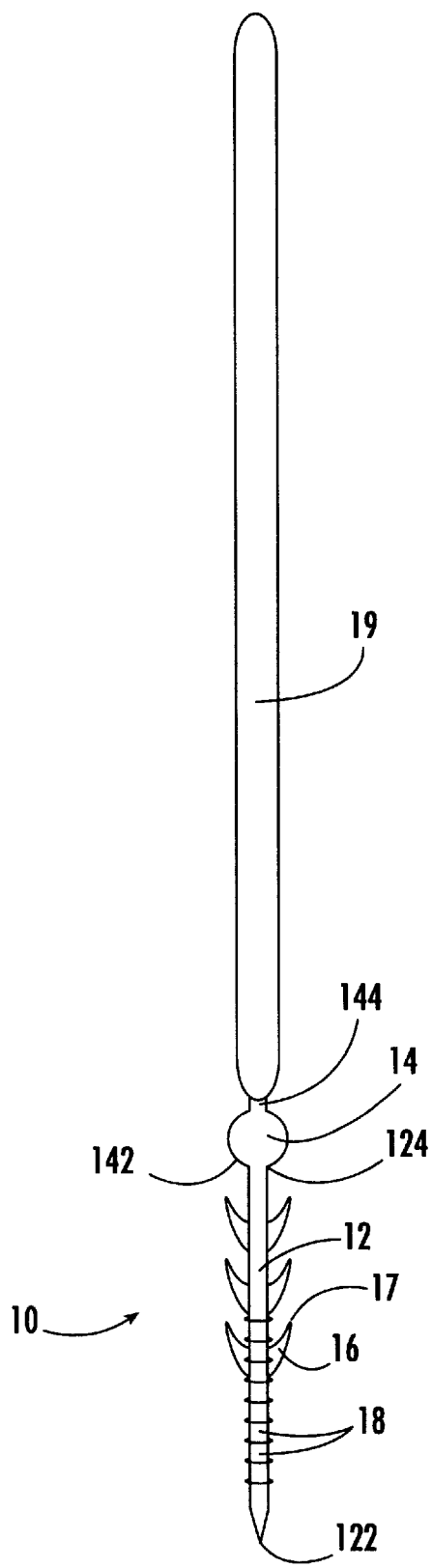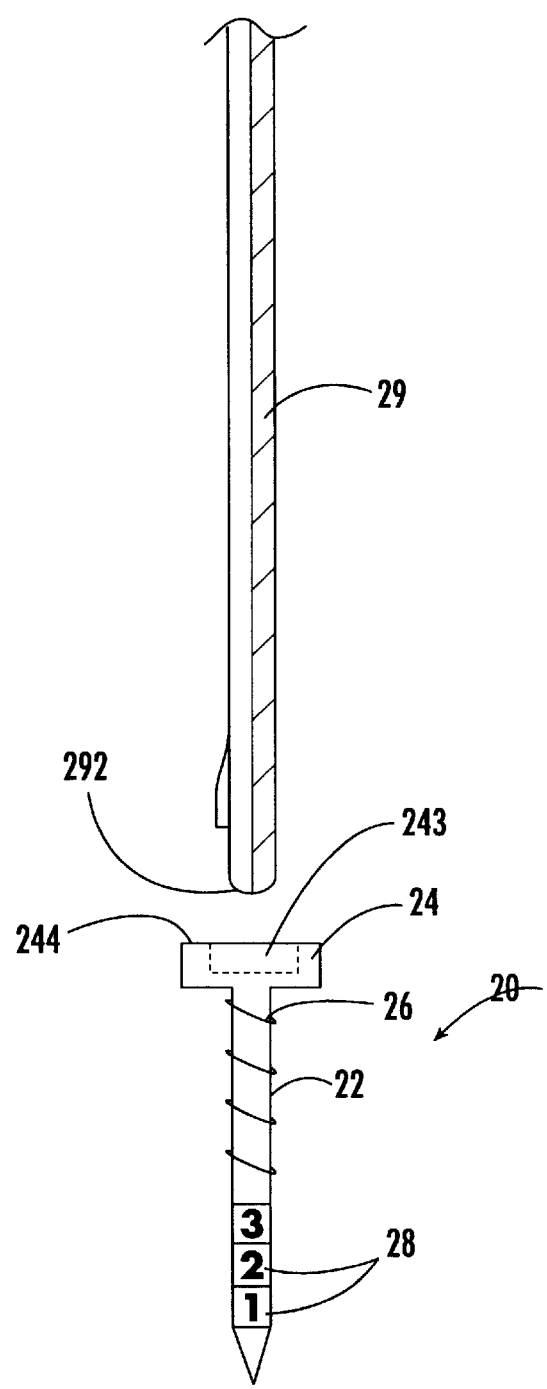
FIG. 1.
FIG. 3.

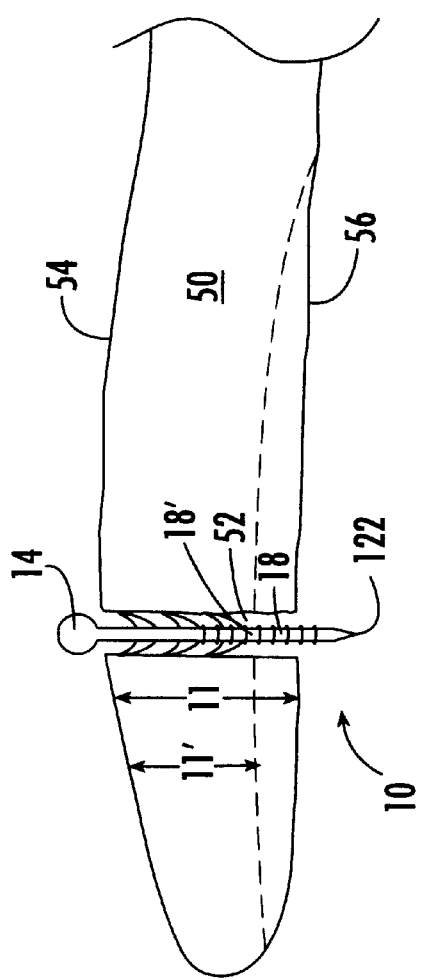
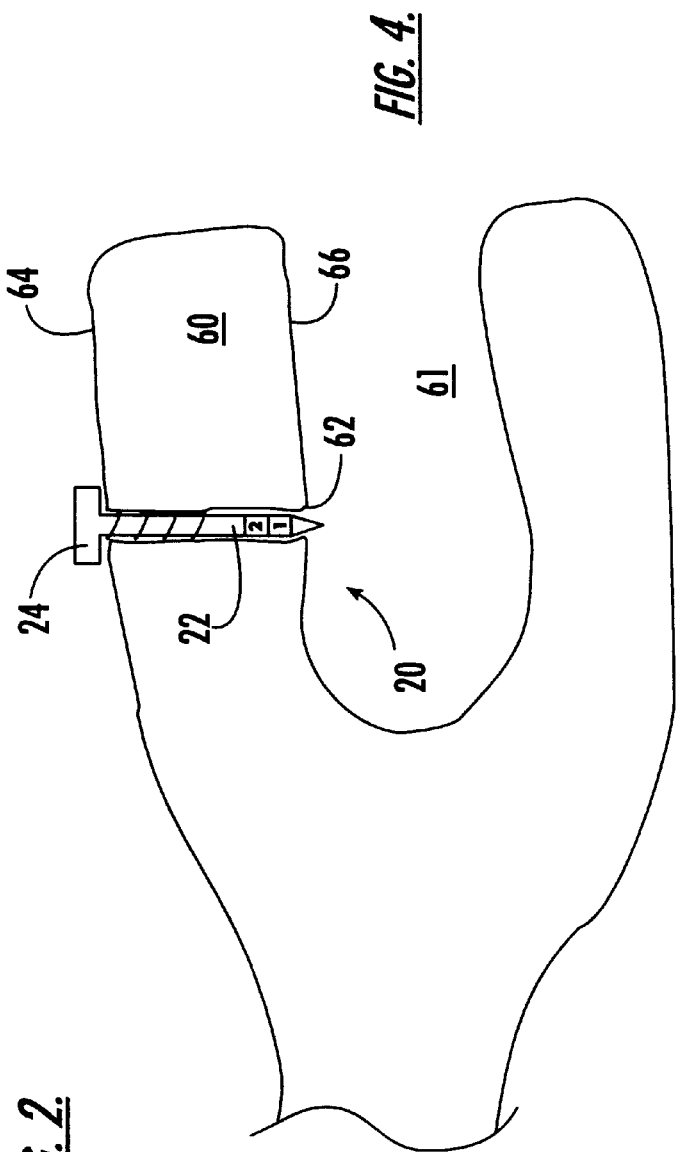

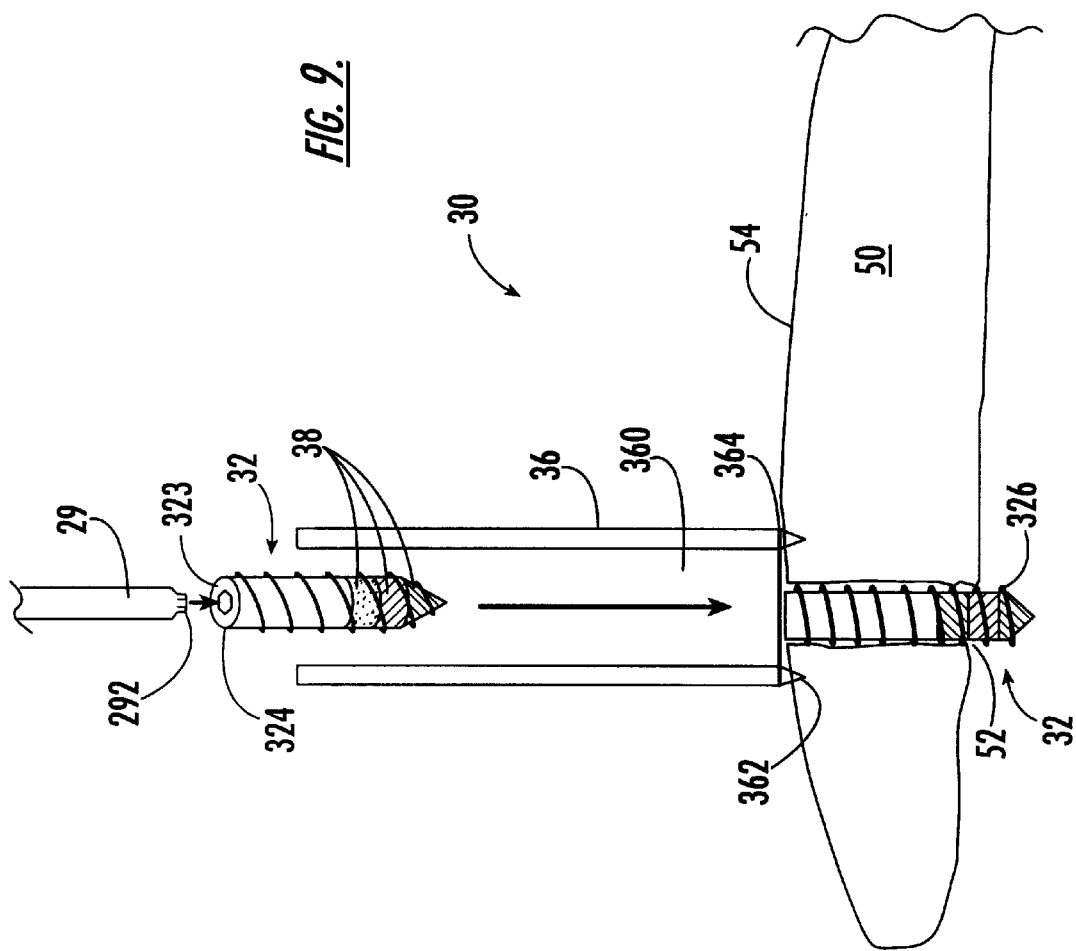

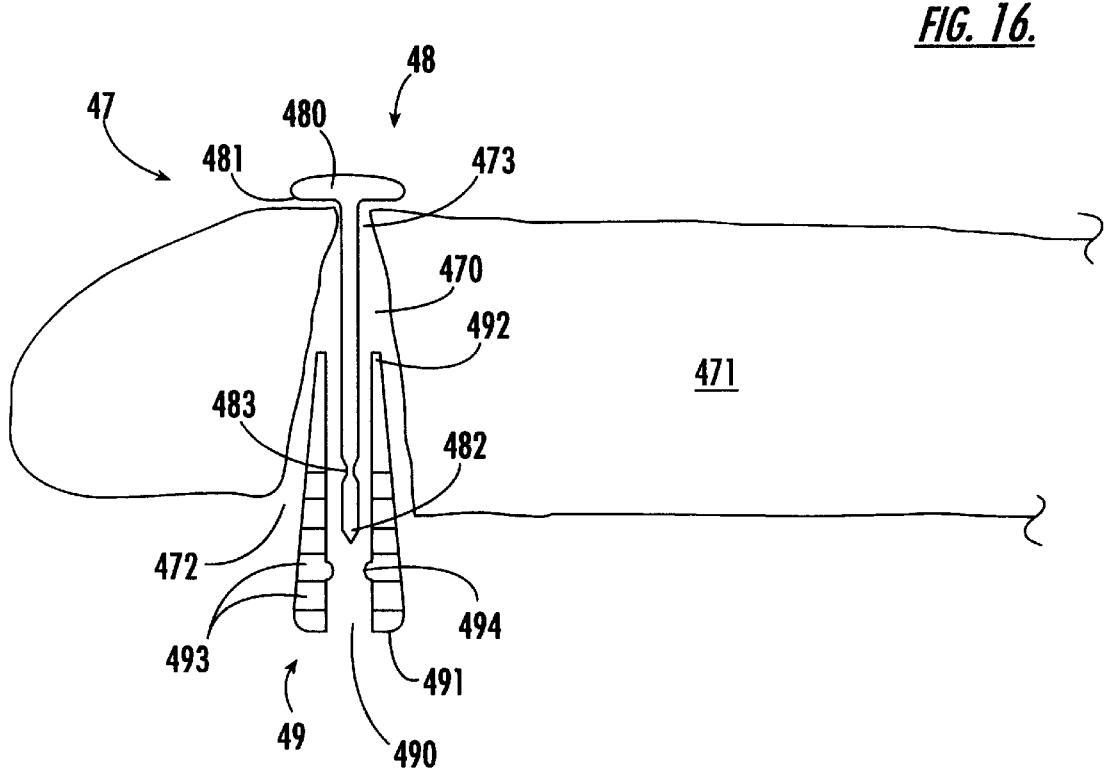

BONE DEPTH RESECTION GUIDE AND METHOD

CROSS-REFERENCE TO RELATED APPLICATION

This application is a continuation-in-part of application Ser. No. 09/205,593, filed Dec. 4, 1998. U.S. Pat. No. 6,042,584.

BACKGROUND OF THE INVENTION

1. Field of the Invention

The present invention relates to devices and methods for resectioning a bone, and, more particularly, to devices and associated methods for gauging resection depth.

2. Description of Related Art

In arthroscopic surgical procedures for alleviating joint damage, it is typical to remove a portion of a bone. An exemplary procedure is that undertaken to correct impingement syndrome in the shoulder, when the subacromial space in the rotator cuff is tight, or if a spur or downward curvature is present in the acromion. Bone may also be thinned preparatory to attaching a soft tissue graft, such as in anterior cruciate ligament replacement surgery, wherein 5–7 mm of the lateral femoral condyle may be removed to avoid impingement on the ligament graft.

At present there is no known method of determining precisely how much bone should be removed, nor of gauging how much bone has been removed during the procedure. As these procedures are performed through the limited perspective available from arthroscopy, further limited by its monocular nature, depth perception is compromised. Consequently, a surgeon may remove an insufficient amount of bone, possibly mis-sizing, resulting in an impingement problem, or may oversize, creating an inadequate fit, potentially leaving the patient with too little bone mass and with a susceptibility to subsequent fracture.

Other situations also require a knowledge of bone thickness: for gauging bone removal in an osteomyelitis procedure, during reaming of long bones having intramedullary fractures, and for cortex thinning prior to insertion of stemmed arthroplasty components. There is currently no device or method for measuring bone thickness for any of these applications.

SUMMARY OF THE INVENTION

It is therefore an object of the present invention to provide a device for gauging bone thickness during a surgical procedure.

It is an additional object to provide such a device for use in arthroscopic procedures.

It is a further object to provide such a device that is biocompatible.

It is another object to provide such a device that is bioresorbable.

It is yet an additional object to provide such a device that provides a continuous indication of bone thickness.

It is yet a further object to provide a system for measuring a bone shape.

It is yet another object to provide a system for contouring a bone to a desired shape.

An additional object is to provide a method of gauging bone thickness during a surgical procedure.

A further object is to provide a method of deploying a bone thickness gauge during a surgical procedure.

Another object is to provide a method for contouring a bone to a predetermined shape.

Yet an additional object is to provide a method of defining an anatomical boundary for an arthroscopic procedure.

These objects and others are attained by the present invention, a bone depth gauge and methods of using. The gauge, which is for measuring bone thickness, includes an elongated pin for insertion into a bore through a bone section slated for resection. The pin has a length sufficient to span the entire bone section with a distal tip protruding therefrom. Additionally, the pin comprises a material that is excisable along with the bone material The pin further has a length measurement indicator disposed along at least a portion of an outer surface, such as, but not limited to, a series of colored bands or indicia, the visualization of which communicates bone thickness.

The gauge also has a head affixed at a proximal end of the pin, and preferably coformed therewith, which is dimensioned to prevent its movement into the bone section's bore. In a particular embodiment a protrusion, such as a barb or screw thread, extends from the pin's outer surface to assist in retaining the pin within the bore.

In another embodiment the gauge comprises a headless pin that is insertable through a cannula placed at the bone surface adjacent a predrilled hole. In other respects the pin is substantially identical.

Methods utilizing gauges as described above are valuable in arthroscopic procedures, for example, in resectioning an anterior corner of an acromion to relieve effects of tight tolerances in the rotator cuff area of the shoulder. Another exemplary use is in notchplasty, such as in the removal of bone material from the medial wall of the lateral femoral condyle preparatory to anterior cruciate ligament replacement in the knee. Yet another exemplary use is in reaming a bone canal to remove bone and/or cement material.

A further method includes utilizing a plurality of at least one of the types of above-described gauges disposed about a section of bone to permit the contouring of the bone to a predetermined shape, with each gauge being visualized to ascertain a bone thickness at a plurality of points about the bone section.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side perspective view of a bone thickness gauge.

FIG. 2 is a side cross-sectional view of the bone thickness gauge inserted into a bone for use in depth resection.

FIG. 3 is a side perspective view of an alternate embodiment of a bone thickness gauge.

FIG. 4 is a side cross-sectional view of the bone thickness gauge inserted for use in notchplasty.

FIG. 9 is a side cross-sectional view of an alternate embodiment of the bone thickness gauge inserted through a cannula into a bone for use in depth resection

FIG. 16 is a side cross-sectional view of a two-part, interlocking bone thickness gauge system.

DETAILED DESCRIPTION OF THE PREFERRED EMBODIMENTS

Figure 5:
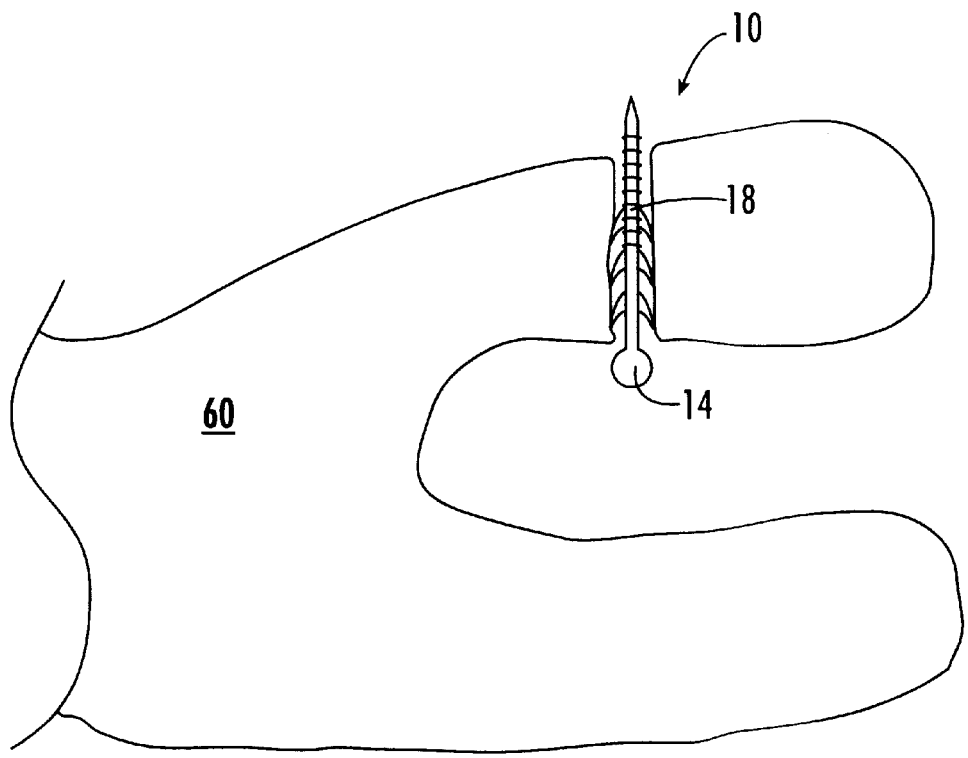
FIG. 5 is a side cross-sectional view of the bone thickness gauge of FIG. 1 inserted for use in notchplasty, with resectioning beginning from the gauge's head region.

A description of the preferred embodiments of the present invention will now be presented with reference to FIGS. 1–16.

A first embodiment of the bone depth gauge 10 for measuring bone thickness is illustrated in FIGS. 1 and 2. Preferably the gauges of the present invention comprise a biocompatible material; more preferably, the gauges comprise a bioresorbable material. In another embodiment the gauge comprises a porous, biocompatible material adapted to encourage bone regrowth therearound and thereinto. The gauge 10 comprises an elongated pin 12 dimensioned to be inserted through a bore 52 in a section of bone 50. The pin 12 is sufficiently long that its distal tip 122, typically pointed, protrudes from the bone's distal face 56.

Figure 8:
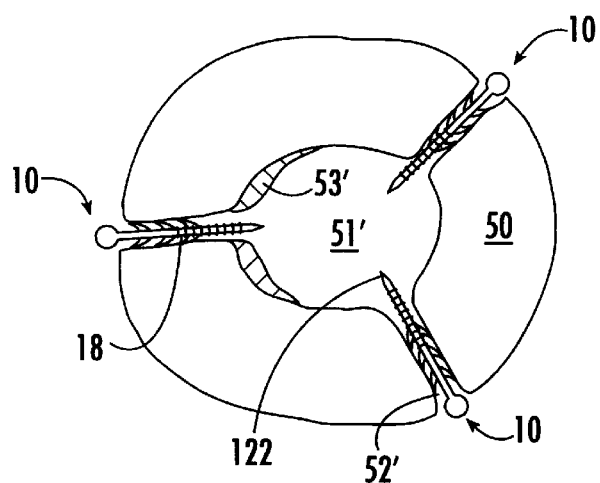
FIG. 8 is an axial cross-sectional view of a plurality of bone thickness gauges inserted into a bone canal preparatory to reaming the canal.
Figure 8A:
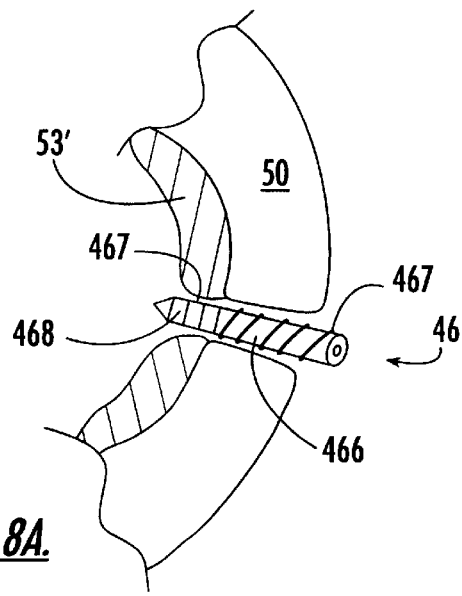
FIG. 8A is an axial cross-sectional view of a partially threaded bone thickness gauge inserted into a bone canal as in FIG. 8.

In another related embodiment the pin 12 is dimensioned to be inserted through a bore 52' into a bone canal 51' of a bone 50' (see FIGS. 8 and 8A).

In a preferred embodiment the pin's outer surface comprises means for resisting removal of the pin 12 from the bone section's bore 52. Such means may comprise, for example, barbs 16 disposed along the outer surface, the barbs having tips 17 directed in a generally proximal direction, so that, once inserted, the barbs 16 resist a pulling force out of the bore 52.

A head 14 is affixed at the pin's proximal end 124, and is dimensioned to prevent its movement into the bone bore 52 from the bone's proximal face 54. Preferably the head 14 has a shape expanding outward from its distal end 142, such as a flared shape, which serves to minimize measurement errors caused by misalignment, although this is not intended as a limitation. The head may also comprise, for example, a round or parabolic shape.

In one embodiment of the invention, in order to facilitate insertion, the head's proximal end 144 is frangibly affixed to an elongated drive member 19, which is generally coaxial with the pin 12 and extends in a proximal direction. In use, the drive member 19 is used to insert the gauge 10 into the bone bore 52, and, when the head 14 contacts the bone's proximal face 54, is broken off and discarded. The drive member 19 is typically preferred since soft tissue may need to be traversed before reaching bone.

In other embodiments the head's proximal end 144 may comprise a noncircular depression for being driven with a commensurately shaped driver, such as a hexagonal-shaped depression for being driven with a hex driver. Alternatively, the gauge 10 may be driven by a device such as a staple gun.

Means are provided on the outer surface of the pin 12 for indicating a length measurement along the pin's longitudinal axis. Such an indicator may comprise, for example, a plurality of successive distinctive, generally circumferential, bands 18, such as bands 18 having different colors, as in a rainbow progression. For this embodiment, the user is provided with a color chart against which to compare a colored band with a depth value.

In use, then, the surgeon would visualize the protruding distal tip 122 of the pin 12 and note the color of the band 18 closest to the bone's distal face 56. Typically the protruding distal tip 122 will be excised in order to avoid losing a piece of pin 12 during bone material removal. Knowing precisely the thickness 11 of the bone 50 at this point, the surgeon could then determine to remove bone material and pin material until a desired thickness 1' is reached, at which point a band 18' of a different color would be visible (shown as a dashed line in FIG. 2). With this device and method, it can be seen that the surgeon is permitted to resect the bone 50 to a predetermined desired thickness.

Figure 13:
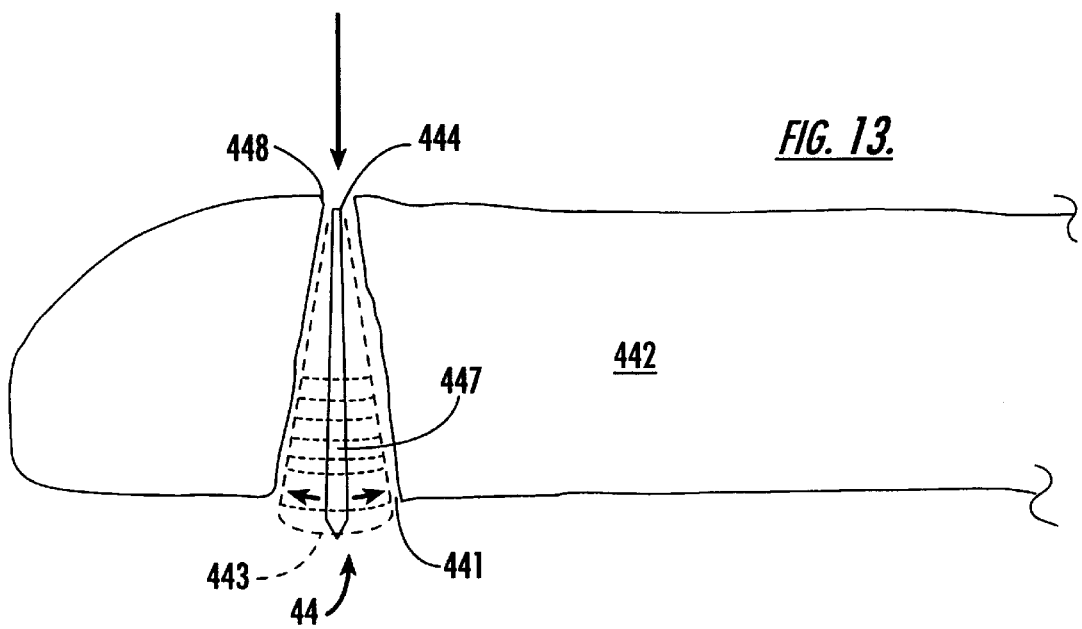
FIG. 13 is a side cross-sectional view of a bone thickness gauge that is deployable within a wedge-shaped bore.
Figure 14:
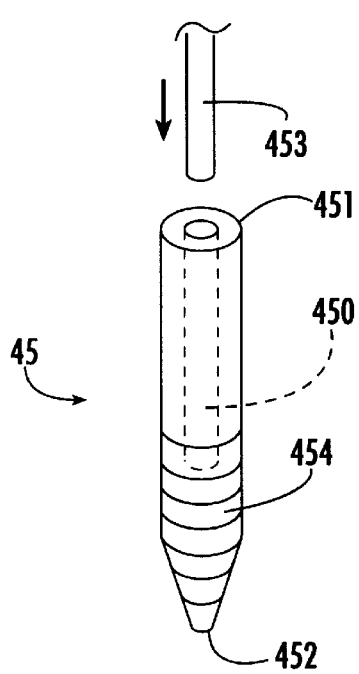
FIG. 14 is a side perspective view of a cannulated bone thickness gauge for inserting into a bone bore.
Figure 15:
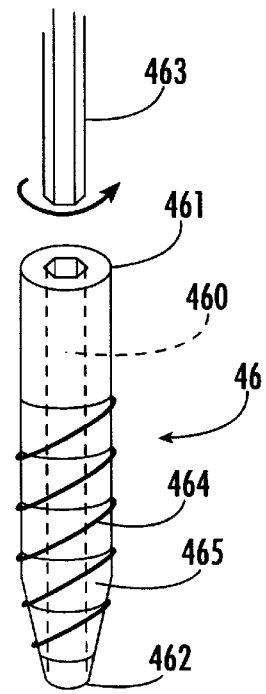
FIG. 15 is a side perspective view of a cannulated bone thickness gauge for screwing into a bone bore.

Another embodiment of a depth gauge 44, shown in FIG. 13, is for insertion into a bore 441 in a bone 442 that can become wider at a distal end 443 than at a proximal end 444. Here the pin 44 has a shape that is expandable and retractable between an elongated insertion shape (full lines in FIG. 13) for introducing the pin 44 into the bore's proximal end 448 and a resection shape (dashed lines, FIG. 13) flaring outwardly from the proximal end 444 to the distal end 443. Again a plurality of successive distinctive generally circumferential mutually differentiable bands 447 are disposed along at least a distal portion of the outer surface of the pin 44 to provide a length measurement. To this end the pin 44 may comprise a compressible material or a hygroscopic material, although these are not intended to be limiting.

In a second embodiment, illustrated in FIGS. 3 and 4, the bone depth gauge 20 has a pin 22 similar to that described above, except that the means for resisting removal comprises a screw-type thread 26 disposed along at least a portion of the pin's outer surface. In this case the drive member 29 would permit a screwing-type motion for insertion, such as into a bore 62 into a femoral condyle 60 from a proximal face 64 through to a distal face 66 into the notch 61. The bone depth gauge 20 also has a head 24, here a flat head 24, with a hex-shaped depression 243 in the head's proximal face 244. Such a gauge 20 is then drivable with a screwdriver-type device 29 having a commensurately shaped distal end 292 for insertion into the depression 243.

The indicator means in this embodiment comprises a plurality of successive indicia disposed along the pin 22, for example, a series of numbers 28. Such numbers 28 may be disposed along an outer surface of the pin 22. Alternatively, the pin's distal portion may comprise a transparent material, such as a plastic, which has the numbered indicia embedded therein. The numbers 28 exposed beneath the tissue are visualizable therethrough via the magnification available in arthroscopy.

Similarly, the indicia may comprise a series of visually distinguishable patterns. For example, the patterns could comprise textures such as ribbed, meshed, dotted, etc., as are known to those of skill in the art. In this embodiment a chart would be provided to correlate depth with exposed texture band.

In a third embodiment, either of the above gauge embodiments 10 or 20 can be resected from the opposite end. As illustrated in FIG. 5 for gauge 10, it may be more convenient in some procedures to insert a gauge 10 so that the head 14 is located at the desired bone-removal site, such as in notchplasty of bone 60. In this case, then, the indicia bands 18 are visualized starting from the head 14, with the surgeon referring to a chart that is the inverse of that described above to read off a resection depth value. This embodiment also permits, for example, a resectioning of an acromion from the bottom, without requiring an additional portal.

Figure 10:
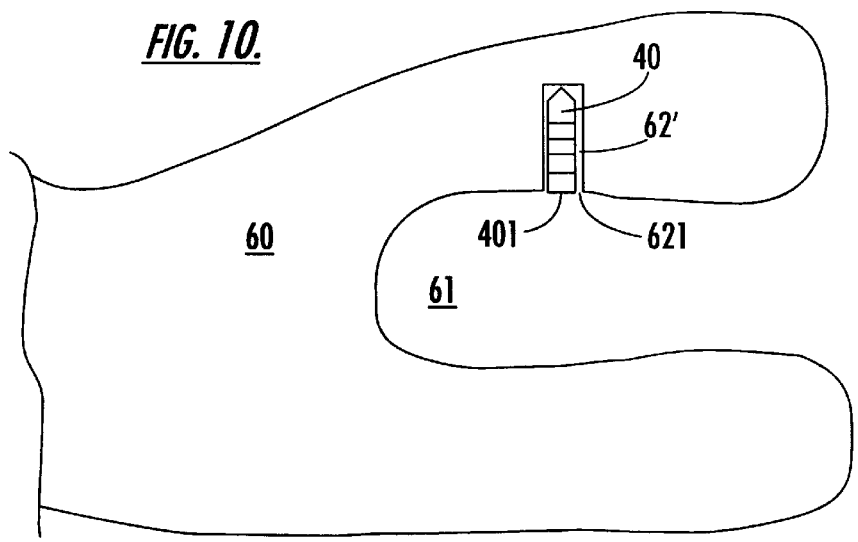
FIG. 10 is a side cross-sectional view of a bone thickness gauge inserted for use in notchplasty, with resectioning beginning from the gauge's proximal end.

An alternate to the third embodiment, shown in FIG. 10, comprises a bone depth gauge 40 that is insertable into a bore 62' in a bone 60 that does not necessarily extend completely through the bone 60. In this case the gauge 40 only need be sufficiently long to enter and remain in the bore 62'. Resectioning proceeds from the proximal end 401, with the amount resected determined from the proximalmost indicator means, such as colored band, number, or other distinguishably marked surface, visible at the bore's proximal end 621.

Figure 12:
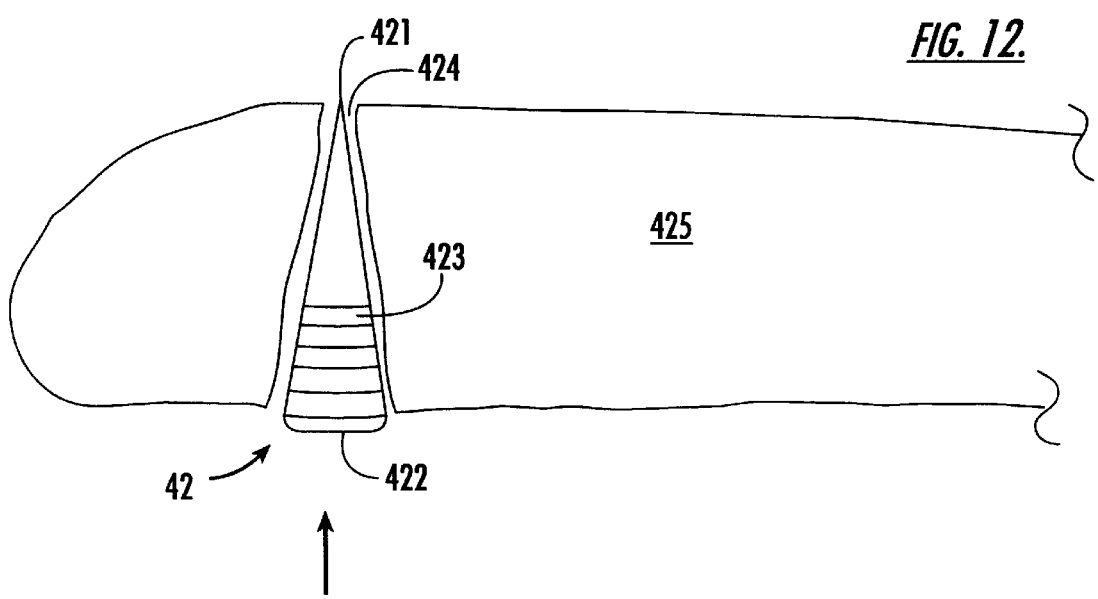
FIG. 12 is a side cross-sectional view of a wedge-shaped bone thickness gauge insertable from the distal face of the bone.

Another alternate to the third embodiment, shown in FIG. 12, comprises a bone depth gauge that comprises a pin 42 that has an outwardly flaring shape from the distal end 421 to the proximal end 422. Here the bands 423 are disposed along at least a proximal portion of the pin's outer surface to provide a length indication. For example, the pin 42 shown here has a generally wedgelike shape, inserted into a commensurately shaped bore 424 in a bone 425. Such a shape will provide greater resistance to the pin's being pushed through a bone during resection and would also provide greater stability in situations such as osteoporotic bone. Another advantage to this design is that the narrower distal end 421 is inserted into an area of the bone that is not being resected, which means that a smaller defect has been made in that region of the bone that will remain following the procedure. A particular application of this pin 42 includes a subacromial placement, although this is not intended to be limiting.

Figure 6:
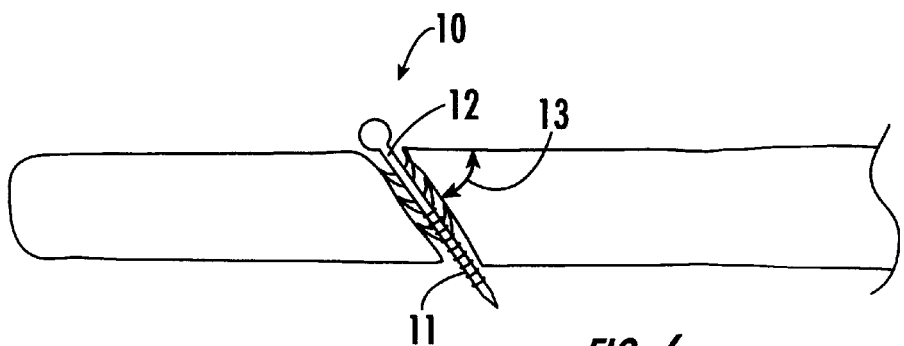
FIG. 6 is a side cross-sectional view of a radio-opaque bone-thickness gauge inserted at an angle to the bone face.

In a fourth embodiment, a gauge comprises radio-opaque material so that it may be visualized radiographically following insertion. As illustrated in FIG. 6 for gauge 10 with a radio-opaque coating 11, insertion may not always proceed normal to the bone surface, which may or may not be intentional. The ability to noninvasively visualize the angle 13 described by the pin 12 section, however, still provides the surgeon with sufficient information to determine resection depth. A trigonometric chart would be provided so that the surgeon could, knowing the angle 13, determine how the indicia bands 18 correlate with a depth perpendicular to the bone surface.

Figure 11:
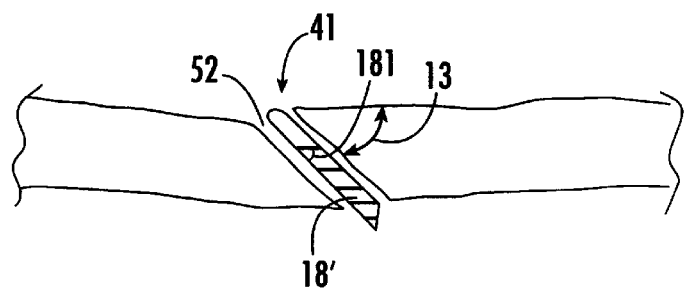
FIG. 11 is a side cross-sectional view of a bone thickness gauge having angled bands.

An alternate to the fourth embodiment comprises a gauge 41 that would not require a chart for interpretation (FIG. 11). In this gauge 41 the indicia bands 18' are already placed at the same angle 181 as that 13 of the bore 52, and the length indication is directly interpretable from the bands 18'.

In a fifth embodiment, illustrated in FIG. 9, a resection system 30 is provided that comprises a pin 32. Here the means for resisting removal comprises a screw-type thread 326 disposed along at least a portion of the pin's outer surface, in this particular embodiment disposed along the entire length of the pin 32. This pin 32, however, is headless, but has a hex-shaped depression 323 at the proximal end 324. Such a pin 32 is then drivable with a screwdriver-type device 29 having a commensurately shaped distal end 292 for insertion into the depression 323.

Means are again provided on the outer surface of the pin 32 for indicating a length measurement along the pin's longitudinal axis. Such an indicator may comprise, for example, a plurality of successive distinctive, generally circumferential, bands 38, such as bands 38 having different colors, as in a progression wherein adjacent colors are readily distinguishable from each other (e.g., red to green to purple to yellow, etc.). Alternatively, the entire pin 32 may comprise the progressive colors therethrough, that is, the pin 32 comprising stacked colored discs, so that the exposed distal surface displays the same color as the band 38 as it is resected along with bone material. For these embodiments, the user is again provided with a color chart against which to compare a colored band with a depth value.

Alternately, as above, the bands 38 may comprise stacked discs of differing textures, with the user provided with a chart correlating texture type with depth value. The bands 38 may also comprise numbered indicia, either along the surface of the pin 32 or embedded within a substantially transparent material.

Although the embodiments of the depth gauge thus far discussed may be composed of any suitable material that can be resected along with the bone, it would be preferable that the gauge be resectable with an implement such as a burr without occluding or dulling the cutting surface. More preferably, the gauge should have the same resection characteristics as the adjacent bone. If the gauge requires a substantially different amount of pressure from the bone to resect, dislodgement may occur and the necessary depth reference lost. Therefore, another embodiment is considered.

In this sixth embodiment, the pin has an elongated bore that may extend longitudinally from the proximal end to the distal end or may comprise a partial bore extending just from the proximal end. In a first case (FIG. 14) the pin 45 comprises a generally cylindrical member having a bore 450 extending from the proximal end 451 and ending prior to the distal end 452. This bore 450 permits the pin 45 to be driven from the proximal end 451 by an elongated driving device 453 having a distal portion insertable into the bore 450. Such an embodiment has the benefit of providing additional stability and strength to the pin 45 during insertion, permitting the use of a material that is suitable for resection along with the bone. Bands 454 are disposed along at least a distal portion of the pin 45.

A related embodiment includes a pin 46 (FIG. 15) comprising a member that is at least partially threaded 464 having a bore 460 extending at least from a proximal end 461, and possibly completely through to the distal end 462. Bands 465 are disposed along at least a distal portion of the pin 46. This bore 460 has a noncircular cross section along at least a section thereof, in order to permit being driven by a driver 463 having a shape adapted for rotating the pin 46. Again, this embodiment provides stability and strength to the pin 46 during insertion.

System 30 further comprises a means for introducing the pin, such as pin 32, into a desired site, such as across a bone section. A particular means comprises a cannula 36 that is adapted to channel the pin 32 through its bore 360 into a predrilled hole 52 in a bone 50. The bore 360 is also sufficiently large to permit the driver 29 to pass thereinto from the proximal end 361. In use, the driver 29 is engaged with the pin 32 and is rotated until the pin's proximal end 324 is generally flush with the bone surface. This feature permits a generally smooth bone surface to be maintained following the procedure, with the pin 32 left in place.

The cannula 36 includes means for removably attaching to the bone's proximal surface 54, such as prongs 362 at the distal end 364 to stabilize the cannula 30 during insertion of the pin 32. The cannula 30 provides added stability to the pin 32 during its insertion.

Yet another embodiment comprises a bone depth measurement system 47 for insertion into a bore 470 through a bone section 471 to be resected (FIG. 16). Here the bore 470 flares outwardly from a proximal end 472 to a distal end 473. The system 47 comprises two interlocking pieces. The first piece comprises an elongated pin 48 that has a head 480 at a proximal end 481 and a length sufficient to span the entire bone section 471 with a distal tip 482 protruding therefrom. The pin 48 also has a distal portion that comprises a material that is excisable with the bone material.

Figure 7:
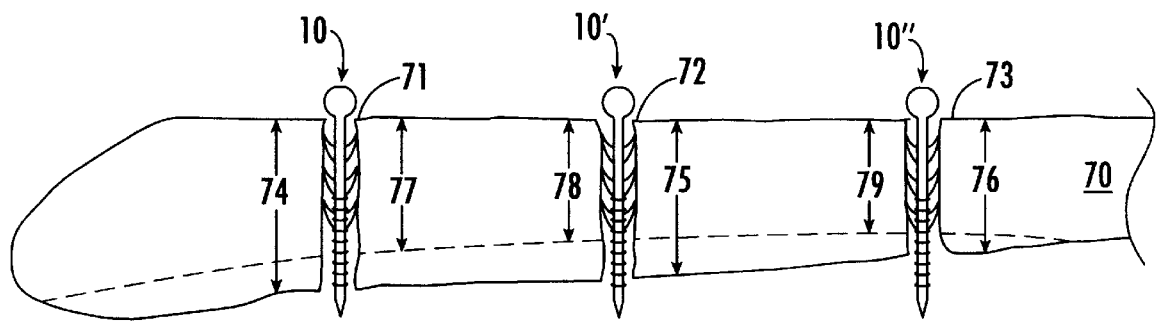
FIG. 7 is a side cross-sectional view of a plurality of bone thickness gauges inserted into a bone for use in contouring a bone.

The second piece comprises a wedge-shaped covering member 49 that has a flared shape wider at a distal end 491 than at a proximal end 492. The wedge 49 has a plurality of successive distinctive generally circumferential bands 493 disposed along at least a distal portion of an outer surface of the wedge 49 for providing a length indication A bore 490 extends from the distal end 491 through to the proximal end 492. The bore 490 is dimensioned to admit the pin's distal portion from the wedge's proximal end 492. The two pieces are interlockable together so that a precise reference from the pin's head 480 to the wedge's distal end 491 is calculable. Such interlocking may be achieved, for example, by commensurate notches 483,494 in the pin 48 and wedge 49, respectively. In surgery, the system 47 is used by inserting the pin 48 into the bone's bore 470 from the proximal end 472 until the head 480 rests against the bone 471. Then the wedge 49 is inserted into the bone's bore 470 from the distal end 473, with the wedge's bore over the pin's distal portion until the notches 483,494 interlock. This system 47 provides a good length reference via the bands 493 from the proximal surface of the bone 471, since the interlocking pieces 48,49 when engaged provide a known spanning length; further, the shape of the wedge 49 provides added stability during the resectioning process and places the narrowest portion of the gauge system 47 in the portion of the bone that will remain following the procedure While one gauge 10,20,32 may be used to indicate a bone thickness at a particular location, and to provide a continual readout during resectioning, a surgeon may also perform a relatively precise bone contouring procedure with the use of a plurality of gauges, as shown in FIG. 7 for gauges 10. Typically one or more images of the target bone 70 will have been taken prior to the procedure, and the surgeon will have determined a desired bone shape (illustrated as a dashed line in FIG. 7) and a map therefor.

In this method a plurality of gauges, here three gauges 10,10',10" are inserted in three bores 71,72,73 in the bone 70. Owing to the elasticity of the skin and underlying soft tissue, typically a plurality of gauges can be placed through a unitary skin incision, which is a significant benefit. Thicknesses 74,75,76 are determined with the use of the gauges 10,10',10". Resectioning and concomitant pin excision are carried out in stages, such as with a burr or any device known in the art, periodically visualizing the gauges 10,10', 10" to determine current thickness values. This procedure is repeated until the desired thicknesses 77,78,79 at each location are achieved.

Insertion of the gauges 10,20 may be accomplished in a number of ways. In a particular embodiment, a bore is drilled through the bone section and a gauge is inserted thereinto. In another embodiment, a driver is utilized that has elements for creating the bore in one step, such as with a drill having a stop, and then driving the gauge into the bore in another step. Such a device would likely only require a single puncture wound in the patient's skin to deploy a desired number of gauges owing to the skin's elasticity. Alternatively, a device such as a staple gun could be used, as mentioned above, which could be cannulated, as could be used, for example, with system 30.

In yet another embodiment, illustrated in FIG. 8, one of the gauges 10,20,32 can be used to aid in reaming a canal 51' in a bone 50' of bone material and/or cement 53' from an implant. In this case the method includes inserting a gauge, here shown as gauge 10, preferably a plurality of gauges 10, through bore(s) 52' drilled in the bone 50' into the canal 51' and visualizing a distal tip 122 of each gauge 10 protruding into the bone canal 51'. Next a distal portion of the gauges 10 and a portion of bone and/or cement are removed from the canal 51'. As above, it is then determined from the bands 18 how much of the bone and/or cement material has been removed. These steps are then repeated until a predetermined desired amount of bone and/or cement material has been removed.

Illustrated in FIG. 8A is another embodiment of the gauge 46' for this use. Here the pin 46' is threaded along a first, outer portion 466 intended for residing in the bone cortex 50 and is smooth along a second, inner portion 467 for residing in the bone cement 53' so that the threads 467 do not cause the cement 53' to crumble. Again, bands 468 are disposed along at least a distal portion of the pin 46' for guiding the extent of resection.

This method has a number of benefits over previously known surgical techniques: When it is desired to remove only cement from a canal, it is often difficult to differentiate between cement and bone material, and removal of bone stock may be excessive, or a bone may even be perforated, especially in curving bones. This method prevents these problems, and permits retaining a predetermined thickness of bone cortex. This method can also be used to prepare the bone for a cementless implant.

It may be appreciated by one skilled in the art that additional embodiments may be contemplated, including gauges having alternate shapes and indicator means.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A bone depth gauge comprising an elongated pin for insertion into a bore through a bone section to be resected, the pin having:
   a length sufficient to span the entire bone section with a distal tip protruding therefrom;
   a plurality of successive distinctive generally circumferential different-colored bands disposed along at least a distal portion of an outer surface of the pin for indicating a length measurement therealong; and
   means for being driven at a proximal end;
   wherein the pin comprises a material excisable with the bone material.

2. The bone depth gauge recited in claim 1, wherein the pin distal tip is pointed to facilitate insertion through the bone section bore.

3. The bone depth gauge recited in claim 1, wherein the pin comprises a biocompatible material.

4. The bone depth gauge recited in claim 1, wherein the pin comprises a bioresorbable material.

5. The bone depth gauge recited in claim 1, wherein the pin has an appearance sufficiently distinguishable from bone and cement to permit in situ visualization thereof.

6. The bone depth gauge recited in claim 1, wherein the pin comprises a porous, bioresorbable material adapted to encourage bone regrowth therearound and thereinto.

7. The bone depth gauge recited in claim 1, wherein the pin further has means for resisting removal from the bone section bore.

8. The bone depth gauge recited in claim 7, wherein the removal resisting means comprises a screw-type thread disposed along at least a portion of the outer surface.

9. The bone depth gauge recited in claim 7, wherein the removal resisting means comprises a plurality of barbs disposed along the outer surface and having tips directed generally proximalward.

10. The bone depth gauge recited in claim 1, further comprising an elongated drive member frangibly affixed to the pin proximal end and extending proximalward generally coaxially with the pin, for facilitating insertion.

11. The bone depth gauge recited in claim 1, wherein the pin proximal end comprises means for being driven by an elongated drive member.

12. The bone depth gauge recited in claim 11, wherein the means for being driven comprises the pin having a longitudinal bore extending from the proximal end, the bore for admitting an elongated drive member thereinto to facilitate pushing the pin into the bore.

13. The bone depth gauge recited in claim 11, wherein the means for being driven comprises a depression that is noncircular in axial cross section in a proximal face of the pin for being driven by a drive member having a commensurately shaped protrusion at a distal end.

14. The bone depth gauge recited in claim 11, wherein the means for being driven comprises the pin having a longitudinal bore extending from the proximal end, at least a portion of the bore having a noncircular cross section for admitting a drive member having an elongated distal portion adapted for driving the pin into the bone section bore.

15. A bone depth gauge comprising an elongated pin for insertion into a bore through a bone section to be resected, the pin having:
   a length sufficient to span the entire bone section with a distal tip protruding therefrom;
   a plurality of successive indicia disposed along at least a distal portion of an outer surface of the pin for indicating a length measurement therealong; and
   means for being driven at a proximal end;
   wherein the pin comprises a material excisable with the bone material.

16. The bone depth gauge recited in claim 15, wherein the indicia comprise numbers.

17. The bone depth gauge recited in claim 16, wherein the pin distal portion comprises a transparent material having the number indicia embedded therein and visualizable therethrough.

18. The bone depth gauge recited in claim 15, wherein the indicia comprise a series of visually distinguishable patterns.

19. The bone depth gauge recited in claim 15, wherein the bone section bore forms a first angle with a distal face of the bone section and the indicia comprise a series of mutually distinguishable bands, the bands disposed along the pin surface at a second angle generally equivalent to the first angle, the pin positionable within the bore so as to align the bands generally parallel with the bone section distal face.

20. A bone depth gauge comprising an elongated pin for insertion into a bore in a bone section to be resected, the pin having:
   a plurality of successive mutually distinguishable bands disposed along at least a proximal portion of an outer surface of the pin for indicating a length measurement therealong; and
   means for being driven at a proximal end;
   wherein the pin comprises a material excisable with the bone material.

21. The bone depth gauge recited in claim 20, wherein the bands comprise a series of different-colored bands.

22. The bone depth gauge recited in claim 20, wherein each band has an indicium thereon.

23. The bone depth gauge recited in claim 22, wherein the indicia comprise a series of numbers.

24. The bone depth gauge recited in claim 22, wherein the indicia comprise a series of differently patterned bands.

25. A bone depth gauge comprising a pin for insertion into a bore through a bone section to be resected, the pin having:
   an outwardly flaring shape from a distal end to a proximal end; and
   a plurality of successive distinctive generally circumferential mutually differentiable bands disposed along at least a proximal portion of an outer surface of the pin for indicating a length measurement therealong;
   the pin comprising a material excisable with the bone material.

26. The bone depth gauge recited in claim 25, wherein the pin has a generally wedgelike shape.

27. A bone depth gauge comprising a pin for insertion into a bore through a bone section to be resected, the bore wider at a distal end than at a proximal end, the pin having:
   a shape expandable and retractable between an elongated insertion shape adapted for introducing the pin into the bore proximal end and a resection shape flaring outwardly from a proximal end to a distal end; and
   a plurality of successive distinctive generally circumferential mutually differentiable bands disposed along at least a distal portion of an outer surface of the pin for indicating a length measurement therealong;
   the pin comprising a material excisable with the bone material.

28. The bone depth gauge recited in claim 27, wherein the pin comprises a compressible material.

29. The bone depth gauge recited in claim 27, wherein the pin comprises a hygroscopic material.

30. A bone depth measurement system comprising:

a bone depth gauge comprising:

an elongated pin for insertion into a bore through a bone section to be resected, the pin having a length sufficient to span the entire bone section with a distal tip protruding therefrom, a plurality of successive distinctive generally circumferential different-colored bands disposed along at least a distal portion of an outer surface of the pin for indicating a length measurement therealong, and means for being driven at a proximal end, wherein the pin comprises a material excisable with the bone material; and means for facilitating an insertion of the pin through the bone section.

31. The bone depth measurement system recited in claim 30, wherein the inserting means comprises means for guiding the gauge through a hole extending through the bone section and for supporting the gauge during the insertion.

32. The bone depth measurement system recited in claim 31, wherein the guiding means comprises a cannula having a bore therethrough from a proximal end to a distal end, the bore dimensioned to permit the pin to pass therethrough.

33. The bone depth measurement system recited in claim 32, wherein the cannula has means for removably attaching to a bone surface at the distal end.

34. The bone depth measurement system recited in claim 33, wherein the attaching means comprises prong means.

35. The bone depth measurement system recited in claim 32, further comprising means for facilitating an insertion of the pin into the bore.

36. The bone depth measurement system recited in claim 35, wherein the insertion facilitating means comprises an elongated drive member frangibly affixed to the pin at the proximal end and extending proximalward generally coaxially with the pin.

37. The bone depth measurement system recited in claim 35, wherein the insertion facilitating means comprises a power driver for forcing the gauge through the bone section.

38. The bone depth measurement system recited in claim 35, further comprising reference means for translating the indicating means into a depth measurement.

39. The bone depth measurement system recited in claim 38, wherein the reference means comprises a chart for correlating an appearance of each band with a bone depth measurement.

40. A bone depth measurement system for insertion into a bore through a bone section to be resected, the bore flaring from a distal end to a proximal end, the system comprising:

an elongated pin having:

a head at a proximal end;

a length sufficient to span the entire bone section with a distal tip protruding therefrom; and a distal portion comprising a material excisable with the bone material; and a covering member having:

a flared shape wider at a distal end than at a proximal end;

a plurality of successive distinctive generally circumferential bands disposed along at least a distal portion of an outer surface of the covering member for indicating a length measurement therealong;

a bore extending from the distal end through to the proximal end, the bore dimensioned to admit the pin distal portion from the covering member proximal end; and means for achieving a locking engagement with the pin distal portion.

41. A bone contouring system comprising:

a plurality of bone depth gauges, each comprising an elongated pin for insertion into a bore through a bone section to be resected, the pin having a length sufficient to span the bone section with a distal tip protruding therefrom and further having a plurality of successive distinctive generally circumferential different-colored bands disposed along at least a distal portion of an outer surface of the pin for indicating a length measurement therealong, the pin comprising a material excisable with the bone material; and means for disposing the gauges about a predetermined region of a bone, for providing a measurement of bone thickness within the bone region; and means for removing bone material within the bone region, the gauges providing a measurement of remaining bone thickness.

42. A method of removing a predetermined amount of bone material comprising the steps of:

creating a hole through a section of bone desired to be resected;

placing a cannula against a proximal end of the hole;

inserting a bone depth gauge through the cannula and into the bone section, the gauge having an elongated distal pin section having a length greater than a depth of the bone section and length indicating means along at least a distal portion of the pin;

visualizing a distal tip of the gauge protruding from a distal face of the bone;

removing a distal portion of the gauge and a portion of bone from the distal face;

determining from the indicating means on the gauge newly created distal end an amount of the bone section that has been removed;

repeating the visualizing, removing, and determining steps until a predetermined desired amount of bone material has been removed; and removing the cannula from adjacent the bone.

\* \* \* \* \*